US008871072B2

(12) United States Patent
Howell, Jr.

(10) Patent No.: US 8,871,072 B2
(45) Date of Patent: Oct. 28, 2014

(54) FLOW STEP FOCUSING

(71) Applicant: Peter B. Howell, Jr., Gaithersburg, MD (US)

(72) Inventor: Peter B. Howell, Jr., Gaithersburg, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 292 days.

(21) Appl. No.: 13/625,585

(22) Filed: Sep. 24, 2012

(65) Prior Publication Data

US 2013/0075257 A1 Mar. 28, 2013

Related U.S. Application Data

(60) Provisional application No. 61/540,081, filed on Sep. 28, 2011.

(51) Int. Cl.
*B01D 57/02* (2006.01)
*G01N 27/447* (2006.01)
*B01L 3/00* (2006.01)

(52) U.S. Cl.
CPC .... *G01N 27/44795* (2013.01); *B01L 3/502761* (2013.01); *B01L 2200/0652* (2013.01); *B01L 2200/0668* (2013.01); *B01L 2300/0816* (2013.01); *B01L 2400/0415* (2013.01); *B01L 2400/0487* (2013.01); *G01N 27/4473* (2013.01)
USPC ............................. 204/451; 204/453; 204/601

(58) Field of Classification Search
USPC .......................................... 204/450, 451, 601
See application file for complete search history.

(56) References Cited

U.S. PATENT DOCUMENTS

| 4,588,492 | A | * | 5/1986 | Bier | 204/629 |
| 6,277,258 | B1 | * | 8/2001 | Ivory et al. | 204/450 |
| 2005/0224350 | A1 | * | 10/2005 | Sibbett | 204/450 |
| 2006/0086611 | A1 | * | 4/2006 | Curcio | 204/451 |
| 2008/0035484 | A1 | * | 2/2008 | Wu et al. | 204/548 |

OTHER PUBLICATIONS

Balss, K M, D Ross, H C Begley, K G Olsen, and M J Tarlov. 2004. DNA hybridization assays using temperature gradient focusing and peptide nucleic acids. Journal of the American Chemical Society 126, No. 41: 13474-13479.
Huang, Z, and C F Ivory. 1999. Digitally controlled electrophoretic focusing. Analytical Chemistry 71, No. 8: 1628-1632.

(Continued)

*Primary Examiner* — Luan Van
*Assistant Examiner* — Maris R Kessel
(74) *Attorney, Agent, or Firm* — US Naval Research Laboratory; Roy Roberts

(57) ABSTRACT

Flow step focusing isolates and concentrates a molecule of interest by flowing a liquid comprising a molecule of interest through a main channel having an inlet and an outlet with application of a first pressure at the inlet; applying a voltage along the channel during the flowing, wherein the voltage is configured to have a polarity such that it drives the molecule of interest in a direction opposite the flow of the liquid; controlling the first pressure and/or the voltage in a manner so as to trap and concentrate the molecule of interest in a region of the main channel; and removing the concentrated molecule of interest from the channel by recovering a portion of the liquid from a side channel diverging from the main channel, wherein the side channel is maintained at a pressure lower than the first pressure. Also disclosed is an apparatus for such.

10 Claims, 3 Drawing Sheets

(56) References Cited

OTHER PUBLICATIONS

Ivory, C F. 2000. Brief Review of Alternative Electrofocusing Techniques. Separation Science and Technology, 35(11): 1777-1793.
Lin, S L, H D Tolley, and M L Lee. 2005. Voltage-controlled electric field gradient focusing with online UV detection for analysis of proteins. Chromatographia 62, No. 5-6 (September): 277-281.
Petsev, Dimiter N, Gabriel P Lopez, Cornelius F Ivory, and Scott S Sibbett. 2005. Microchannel protein separation by electric field gradient focusing. Lab on a chip 5, No. 6 (June): 587-97.
Wen, J, E W Wilker, M B Yaffe, and K F Jensen. 2010. Microfluidic Preparative Free-Flow Isoelectric Focusing: System Optimization for Protein Complex Separation. Analytical Chemistry 82, No. 4: 1253-1260.

* cited by examiner

FLOW STEP FOCUSING

CROSS-REFERENCE TO RELATED APPLICATIONS

This Application claims the benefit of U.S. Provisional Application 61/540,081 filed on Sep. 28, 2011.

BACKGROUND

Many facets of modern medicine and science depend on the ability to reliably measure the presence and quantity of compounds in solution. It remains difficult to differentiate a signal of interest arising from a single compound in a complex mixture of similar compounds. The problem is particularly severe in biological systems, as a molecule of interest in will often be part of a family of closely related compounds that appear similar (if not identical) to the detector.

Several techniques exist that can separate compounds out of a complex mixture so that they can be measured. Chromatography is a well-known example, wherein a small sample of the mixture is injected into a column of packed separation media-, and flushed through with an appropriate solvent. The compounds dissolved in the sample migrate down the column at different speeds and leave the far end at different times. However, the fractions collected at the end of the column inevitably have a much greater volume than the original sample. Dilution is the price paid for being able to tease the compound of interest away from its interfering relatives. While this tradeoff may be acceptable in many circumstances, when our samples are small, or the compound of interest is already dilute, the dilution of chromatographic separation is a serious problem.

Techniques to both isolate and concentrate solutes for analysis are rarely done because they are often cumbersome, multistep processes. They typically involve a separation step (e.g. chromatography with fraction collection) followed by a laborious concentration step, often involving evaporating or subliming away the solvent. It is seldom done because it costly, time consuming, requires trained technicians, and is difficult to do quantitatively.

Focusing techniques can perform both the isolation and concentration in one step. They most commonly depend upon the molecules in question being subjected to two opposing forces. For example, in gradient electrofocusing, the sample solution flows through a non-uniform electric field. The drag of the flowing fluid provides the first driving force on the molecules, and does not change over the length of the channel. The electric field drives the molecules against the direction of flow, and becomes stronger as they move down the channel. There is a point in the channel where the two driving forces become equal. This is where the molecules will become focused.

Focusing within a flowing channel has be demonstrated using a variety of methods, including electric field gradient focusing (EFGF), temperature gradient focusing (TGF) and isoelectric focusing (IEF). These lack a side channel to allow removal of the concentrated band. A variant of IEF, known as free-flow IEF, allows for a continuous separation (see Wen et al.). In the "free flow" format, focusing is performed perpendicular to the direction of flow. The degree of concentration is necessarily limited because solutes can only spend a finite time in the channel before being flushed out. There is no "trap-and-hold" capability.

BRIEF SUMMARY

In one embodiment, a method of isolating and concentrating a molecule of interest includes flowing a liquid comprising a molecule of interest through a main channel having an inlet and an outlet with application of a first pressure at the inlet; applying a voltage along the channel during the flowing, wherein the voltage is configured to have a polarity such that it drives the molecule of interest in a direction opposite the flow of the liquid; controlling the first pressure and/or the voltage in a manner so as to trap and concentrate the molecule of interest in a region of the main channel; and removing the concentrated molecule of interest from the channel by recovering a portion of the liquid from a side channel diverging from the main channel, wherein the side channel is maintained at a pressure lower than the first pressure.

In another embodiment, an apparatus configured to isolate and concentrate a molecule of interest includes a main channel having an inlet and an outlet; a side channel intersecting the main channel and having a side channel outlet; a first pressure controller operably connected to the inlet and configured for pumping fluid into the inlet; a second pressure controller operably connected to either the main channel outlet or the side channel outlet and configured to apply a pressure or a vacuum thereto; and electrodes at each of the inlet and the outlet operably connected to a voltage controller configured to generate a voltage between the electrodes so as to generate an electric field along the channel.

DETAILED DESCRIPTION

Definitions

Figure 1:
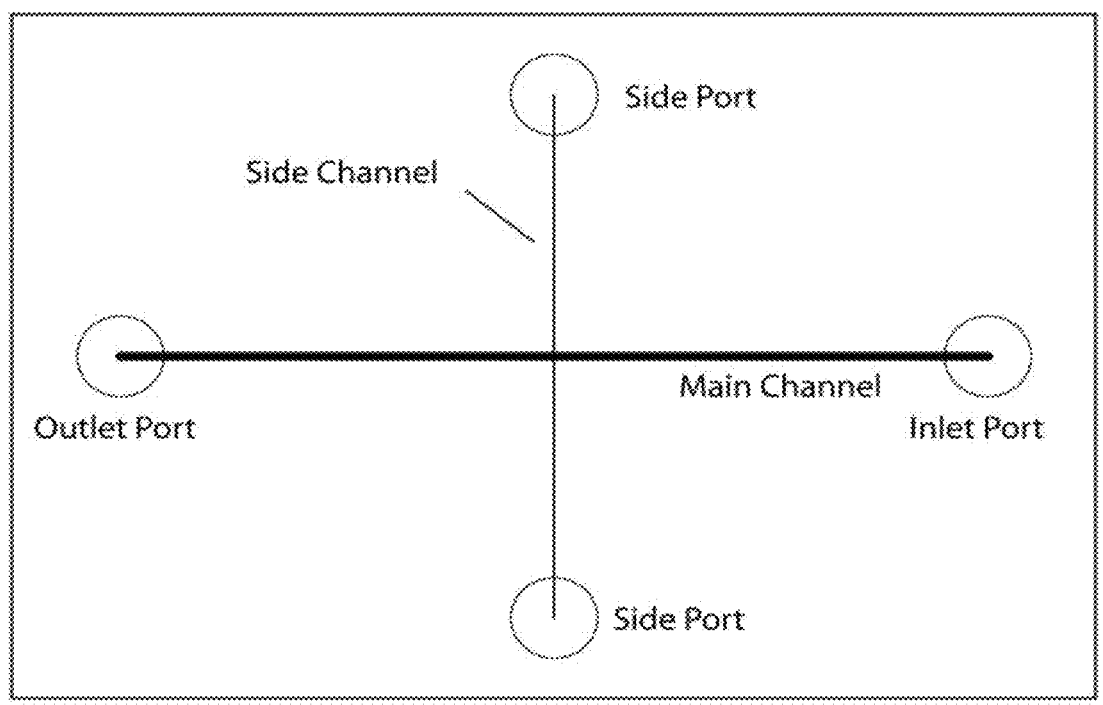
FIG. 1 is a schematic diagram of an exemplary channel configured for flow step focusing.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, the term "molecule of interest" can includes particles, nanoparticles, and cells, as well as molecules. To effectively function as molecules of interest in flow step focusing, they must have a charge, either natively or as provided by complexing them with buffer additives in a liquid.

Description

Flow step focusing is a technique by which a molecule of interest can be both separated and concentrated in a single step. A liquid containing a molecule of interest is driven through a channel (e.g., using a pump) while an electric voltage is applied along the channel. The voltage should have a polarity such that it drives the molecule of interest in a direction opposite the flow of the liquid. With flow velocity higher on the upstream end of the channel than the downstream end, molecules with an electrophoretic velocity in between the upstream and downstream flow velocities will move downstream on the upstream end, and upstream on the downstream end. Thus, molecules of interest become trapped in a narrow region (a "band") within the channel. Over time, the concentration within the region increases as more molecules are added. The position of the band can be adjusted by changing either the voltage or applied pressure (a pressure change operating to change the flow rate). A portion or all of the band can periodically pulled off by moving it across an intersection with a side channel, where fluid is removed from the channel through a side channel outlet.

Operationally, the pressure should be greatest at the inlet of the main channel and lowest at the outlet, with the side channel at an intermediate pressure, regardless of relation to ambient pressure. In the examples, the outlet was at ambient pressure and the other ports pressurized. Alternatively, one could also apply a positive pressure to the inlet and a negative to the outlet, leaving the side at ambient. It is also possible to apply negative pressure (partial vacuum) to the main channel outlet and side channel outlet, leaving the inlet at ambient pressure. Accordingly, the pressure controllers as described herein include those supplying positive and/or negative pressure. As known to a person of skill in the art, resistance can be controlled through the design of main and side channel dimensions as well as through pumps, regulators, and the like.

It is believed that flow step focusing can operate on materials having electrophoretic mobility, to include particles, nanoparticles, and cells as well as molecules dissolved in solution. Such dissolved or suspended materials will either have a charge, or could be given one by complexing them with buffer additives.

The position of the band of interest may be determined using various techniques, such as fluorescence. After the band becomes sufficiently concentrated, other techniques such as optical absorbance or electrical conductimetry could be used. In one embodiment, an automated system receives the position of the band and regulates the pressure and/or the voltage, for example to direct the band towards or away from the side channel.

To find the location of a band, a detector could be employed on the output of the side channel: scanning through electric field strengths and/or flow rates would sequentially proceed band positions past the side channel outlet to be detected. You'll see a spike as each one passes. This embodiment could have applications such as in proteomics, wherein the output is analyzed by, e.g., a mass spectrometer (MS). In a further embodiment, proteins in the output could be digested (such as by passing through a packed bed of immobilized trypsin) so that concentrated bands of proteins are sequentially digested and analyzed by MS for sequencing, identification, and/or quantitation.

EXAMPLES

A proof-of-concept device was fabricated in polymethylmethacrylate (PMMA) using mechanical machining and laser ablation. It included a "cross" intersection of a side channel with a main channel. The main channel was 100 µm wide and 60 mm long. The side channels met the main channel at right angles in its middle. The use of two side channels is optional, and in some embodiments one side channel could be used. In the exemplary device, two side channels were used in to provide robustness against clogging. In some experiments, clogging of one side channel did occur and the experiment continued with only one functional side channel. The side channels were 20 µm wide and 20 mm long. All channels were 20 µm deep. All channels terminated in 6.35 mm diameter wells, accessible from the top. FIG. 1 is a schematic overhead view of an exemplary channel configuration for flow step focusing.

Figure 2:
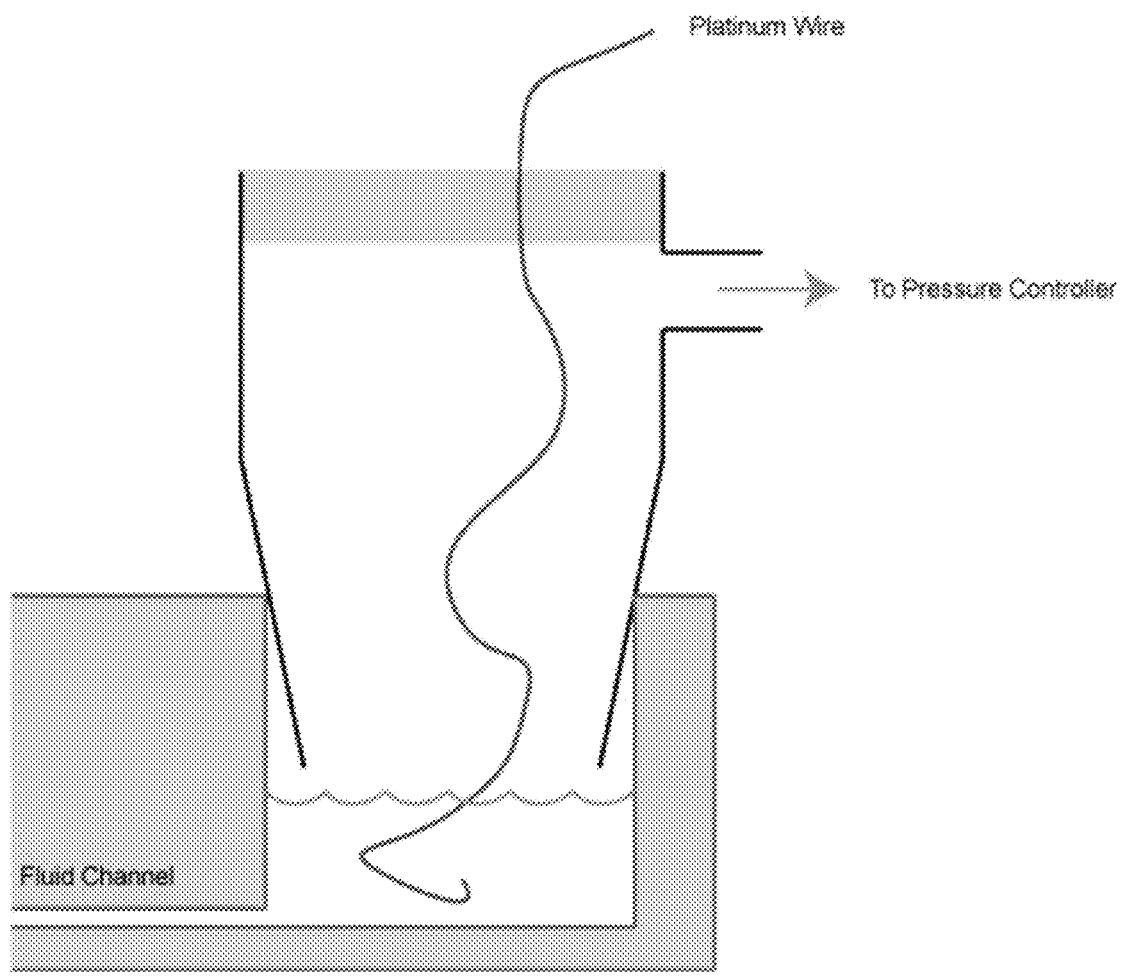
FIG. 2 is a schematic illustration of an exemplary apparatus for flow step focusing.

Well caps were fashioned from pipette tips in an arrangement depicted in FIG. 2. These allowed the airspace over the fluid in each well to be sealed and connected to a pressure controller. The caps on the ends of the main channel were also equipped with a length of platinum wire that hung into the fluid to provide the electrical connections. Pressure was provided via silicone tubing from the outlets of the pressure controllers (Alicat Scientific, Tucson, Ariz.).

A positive voltage was applied to the inlet chamber and the outlet chamber was grounded. The side chambers were allowed to float electrically. A positive pressure was applied to the inlet chamber. The side chambers were connected to a single pressure controller and maintained at a pressure above ambient, but below the inlet pressure. In this way the amount of fluid being removed at the intersection could be carefully controlled. Typical values were inlet pressure of 11 mbar, side channel pressure of 5.7 mbar, outlet at ambient pressure, and 500V applied voltage. No attempts were made to suppress electroosmosis. Instead, pressures were adjusted to counteract it and produce the desired net flows.

Negatively charged solutes undergo electrophoretic migration toward the inlet, but are driven downstream by the bulk flow. Their net velocity is the sum of two velocities: the mean flow velocity downstream and the electrophoretic velocity upstream. At the intersection, a fraction of the bulk flow is lost to the side channels, so that the flow downstream of the intersection is reduced. Under appropriate values of voltage and pressures, there will be a window of mobility in which a molecule of interest will have a net downstream velocity in the region upstream of the intersection and a net upstream velocity in the region downstream of the intersection. As a consequence, the ultimate disposition of that a molecule will be to travel out through the side channel(s).

When the molecule of interest has a mobility that falls within the window, it will become concentrated in the region of the intersection and be pulled out through the side channels. The degree of concentration is simply the ratio of the volumetric flow rates in the main and side channels, respectively, and thus can be controlled.

A different phenomenon occurs when it is one of the buffer components that is selectively removed. Buffer components may be as much as six orders of magnitude more concentrated than the molecule of interest and/or other analytes. When a buffer ion is selectively removed, significant charge separation is quickly established. If, for example, the borate anion is selectively removed from a Tris-Borate buffer, there is a buildup of negative charge in the side channel and a buildup of excess positive charge from the unpaired Tris in the main channel. The electric fields created by the charge separation drive the ions electrophoretically to counteract the selective removal, and an equilibrium state is soon established, where the secondary electric fields prevent the buffer molecule from being continuously removed. The secondary effect of this is to also perturb the electric field in the main channel so that they are no longer uniform. In the non-uniform electric field, it becomes possible to focus solute molecules at any point in a large length of the channel. Because the solutes can be focused well away from the intersection, they are not continuously removed as they enter the concentrated region, and the achievable concentration is no longer limited by the relative flow rates in the two channels. The position of the concentrated band can be moved around by changing either the pressure applied to the inlet channel or the applied field. When the band passes the intersection, it is pulled into the side channel.

Figure 3:
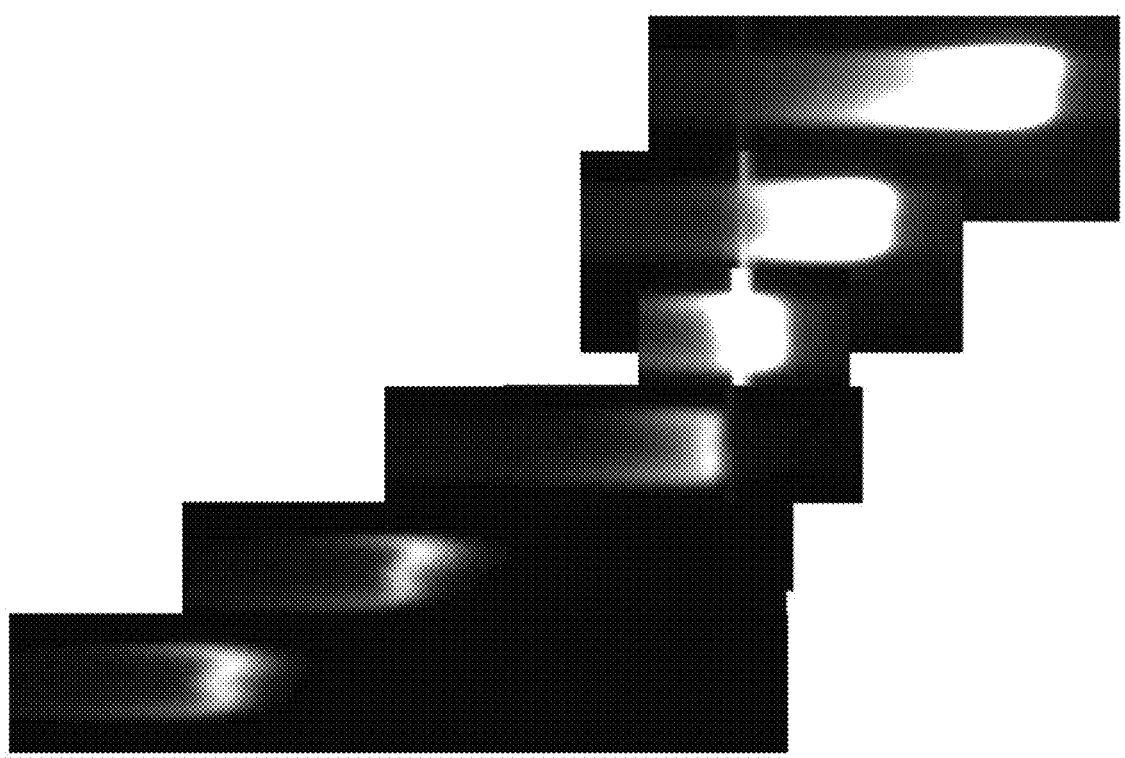
FIG. 3 is a series of images taken sequentially (top to bottom) of a band moving from right to left across an intersection with a side channel.

FIG. 3 is a series of images taken sequentially (top to bottom) of a band moving from right to left across an intersection with a side channel. The initially strong band is reduced as solute is removed at the intersection.

In one embodiment, the system separates solutes based on electrophoretic mobility primarily or entirely. One could alter or enhance the selectivity by adding psuedostationary phases, such as cyclodextrins or micelles. In this way, neutral analytes could be concentrated, and solutes with similar electrophoretic mobility could be separated.

In order to remove the band without perturbing the focusing method, a cross intersection could be used. Solution can be removed from one side channel while an equal amount of replacement buffer is added from the opposite side channel. This prevents a change in the flow velocity as solution passes the intersection, but could be used to change conductivity or other features of the buffering solution The described technique provides several advantages, including:

Simplicity: The system requires only control of voltage and pressure, and requires no moving parts within the "chip" making up the channels. Inexpensive and reliable solenoid valves can be used within pressure controllers to regulate flow.

Adaptability: Unlike free-flow IEF, where solutes flow through the channel at a constant velocity and are only retained briefly before being flushed out, the described technique traps the solutes within a band in the channel until a time such as the band is moved across the intersection. As a result the concentration factor can be adapted by holding the band for varying amounts of time before samples are collected. Significantly, the collection time can be adapted in real time in response to changes in concentration of the sample stream, so that the detection limit and range of a detection system including the device can be adapted to meet the needs of the sample.

Speed: Concentration and purification take place simultaneously, rather than sequentially in a multistep process Cost: The voltage source and pressure supply can be made with current off-the-shelf components.

All documents mentioned herein are hereby incorporated by reference for the purpose of disclosing and describing the particular materials and methodologies for which the document was cited Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Each of the following referenced documents is incorporated by reference herein in its entirety:
Electric Field Gradient Focusing Huang, Z, and C F Ivory. 1999. Digitally controlled electrophoretic focusing. *Analytical Chemistry* 71, no. 8: 1628-1632.

Petsev, Dimiter N, Gabriel P Lopez, Cornelius F Ivory, and Scott S Sibbett. 2005. Microchannel protein separation by electric field gradient focusing. *Lab on a chip* 5, no. 6 (June): 587-97.

Lin, S L, H D Tolley, and M L Lee. 2005. Voltage-controlled electric field gradient focusing with online UV detection for analysis of proteins. *CHROMATOGRAPHIA* 62, no. 5-6 (September): 277-281.

Temperature Gradient Focusing

Balss, K M, D Ross, H C Begley, K G Olsen, and M J Tarlov. 2004. DNA hybridization assays using temperature gradient focusing and peptide nucleic acids. *Journal of the American Chemical Society* 126, no. 41: 13474-13479.

Tang, G Y, and C Yang. 2008. Joule heating induced temperature gradient focusing in a microfluidic channel with a sudden change in cross section. *Proceedings of the Micro/Nanoscale Heat Transfer International Conference* 2008, *Pts a and B:* 179-184.

Isoelectric Focusing

Huang, Z, and C F Ivory. 1999. Digitally controlled electrophoretic focusing. *Analytical Chemistry* 71, no. 8: 1628-1632.

Ivory, C F. 2000. Brief Review of Alternative Electrofocusing Techniques. *Separation Science and Technology,* 35(11): 1777-1793.

Wen, J, E W Wilker, M B Yaffe, and K F Jensen. 2010. Microfluidic Preparative Free-Flow Isoelectric Focusing: System Optimization for Protein Complex Separation. *Analytical Chemistry* 82, no. 4: 1253-1260.

What is claimed is:

1. A method of isolating and concentrating a molecule of interest, the method comprising:
    flowing a liquid comprising a molecule of interest through a main channel having an inlet and an outlet, with application of a first pressure at the inlet;
    applying a voltage along the channel during the flowing, wherein the voltage is configured to have a polarity such that it drives the molecule of interest in a direction opposite the flow of the liquid;
    controlling the first pressure and/or the voltage in a manner so as to trap and concentrate the molecule of interest in a band; and
    removing the concentrated molecule of interest from the channel by recovering a portion of the liquid from a side channel diverging from the main channel, wherein the side channel is maintained at a pressure lower than the first pressure.

2. The method according to claim 1, wherein the removed concentrated molecule of interest is present at a higher concentration than when introduced into the main channel.

3. The method according to claim 1, further comprising replacing the recovered liquid via a second side channel positioned in the vicinity of the side channel.

4. The method according to claim 1, further comprising determining a position of the band via optical fluorescence or absorbance and/or electrical conductivity.

5. The method according to claim 4, wherein an automated system receives the position of the band and regulates said controlling the first pressure and/or the voltage in response thereto.

6. The method according to claim 1, wherein a stationary or pseudostationary phase is incorporated in the channel.

7. The method according to claim 1, further comprising analyzing the recovered portion of the liquid by mass spectrometry.

8. The method according to claim 7, further comprising subjecting the recovered portion of the liquid to proteolysis prior to the analysis.

9. The method according to claim 1, wherein the liquid comprises a buffer.

10. The method according to claim 9, further comprising selectively removing the buffer from the liquid.

* * * * *